United States Patent [19]

Sterling

[11] Patent Number: 4,552,914

[45] Date of Patent: Nov. 12, 1985

[54] HYDROCARBON BLOCK COPOLYMER WITH DISPERSED POLYSILOXANE

[75] Inventor: Robert E. Sterling, New Port Richey, Fla.

[73] Assignee: Medical Research Associates, Ltd. #2, Clearwater, Fla.

[21] Appl. No.: 678,218

[22] Filed: Dec. 4, 1984

Related U.S. Application Data

[62] Division of Ser. No. 465,586, Feb. 10, 1983, Pat. No. 4,511,354, which is a division of Ser. No. 147,475, May 7, 1980, Pat. No. 4,386,179.

[51] Int. Cl.$^4$ .............................................. C08K 5/54
[52] U.S. Cl. ................................... 524/269; 524/490; 524/505
[58] Field of Search ................... 524/269, 490, 505

[56] References Cited

U.S. PATENT DOCUMENTS 4,481,323 11/1984 Sterling ................... 525/92

Primary Examiner—Joseph L. Schofer
Assistant Examiner—N. Sarofim
Attorney, Agent, or Firm—Sherman & Shalloway

[57] ABSTRACT

A composition of matter composed of a thermoplastic elastomeric hydrocarbon block copolymer having 0.1 to 8 percent polysiloxane, or silicone oil, uniformly distributed throughout. The composition exhibits improved surface, elasticity, and tensile strength characteristics as well as superior processability. The block copolymer may take the form of styrene-ethylene-butylene-styrene in which the styrene blocks have a molecular weight of 5,000 to 40,000 and the ethylene-butylene block has a molecular weight of 20,000 to 500,000. Uniformly dispersed mineral oil may constitute 10 to 60 percent of the composition's total weight which may also include less than 45 percent polypropylene. Combining the copolymer with the silicone oil occurs under the influence of a pressure of 1,500 to 2,500 p.s.i. such as provided by extrusion blending. The resulting elastomeric composition may extrude in sheets as thin as 0.015, 0.010, or even 0.005 inch, which a puller may thin even further. The resulting composition has a surface smoothness microscopically characteristic of silicone rubber. As one of its many varied uses, the elastomer may find use as an inflatable cuff or balloon on such medical devices as endotracheal tubes. The high elasticity of the composition permits it to act, when in the trachea, as a high residual volume type endotracheal tube, except that it avoids the folds which permit aspiration fluids to channel to the patient's lungs. The pressure it exerts against the tracheal wall falls even below the high volume device. When not inflated, the material returns to a sufficiently small volume that it acts as a low volume device for ease of insertion and withdrawal.

9 Claims, 17 Drawing Figures

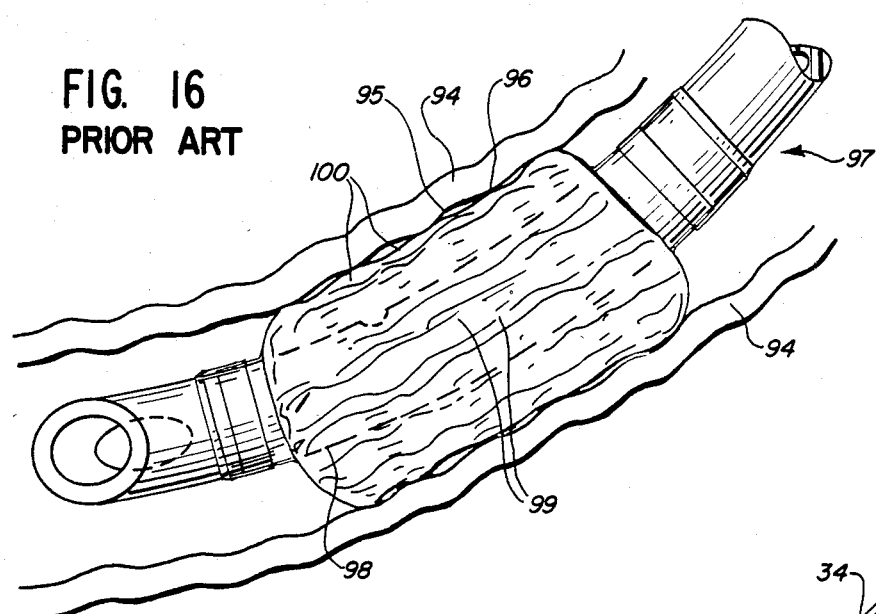
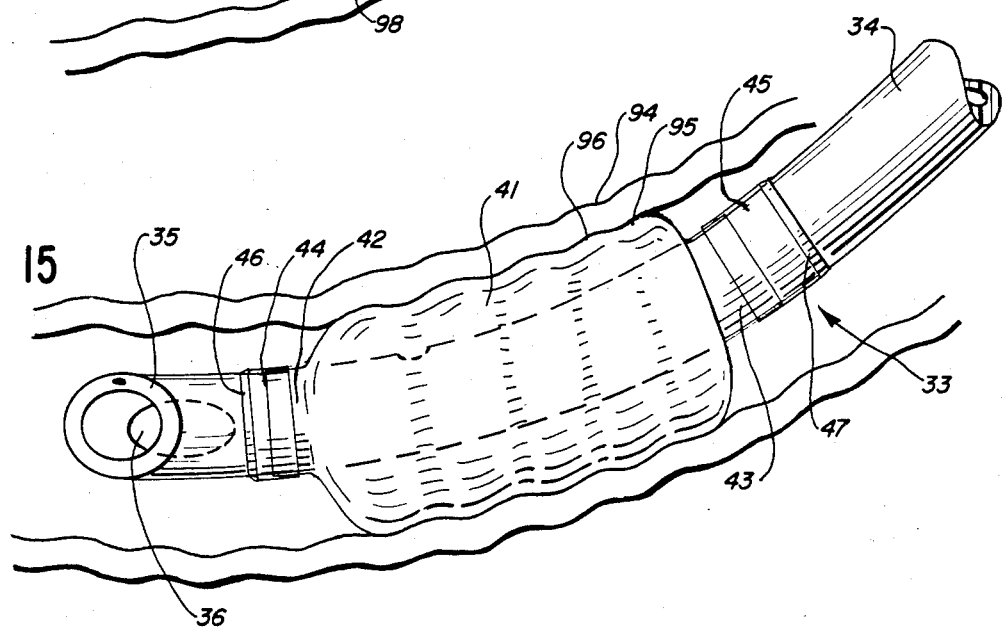
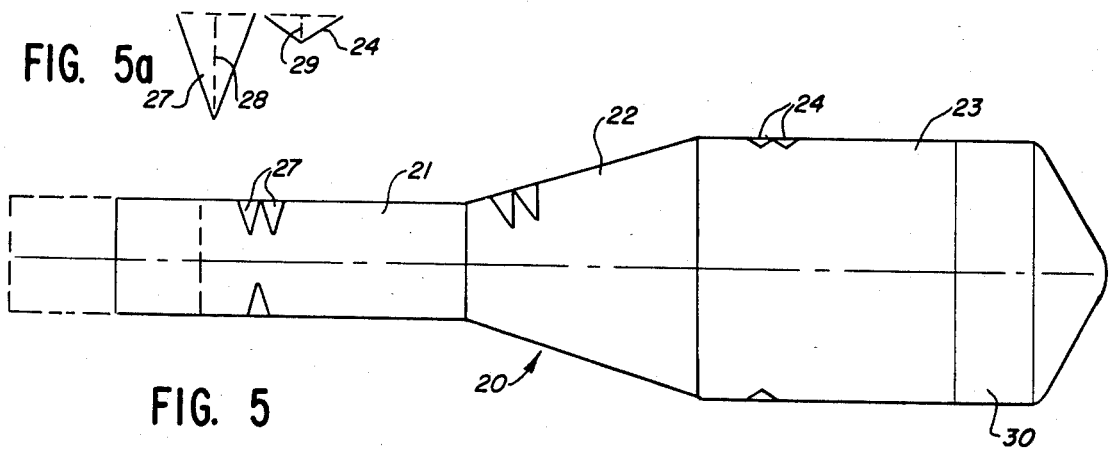

HYDROCARBON BLOCK COPOLYMER WITH DISPERSED POLYSILOXANE

This is a division of application Ser. No. 465,586, filed Feb. 10, 1983, now U.S. Pat. No. 4,511,354, which is a divisional application of Ser. No. 147,475, filed May 7, 1980, new U.S. Pat. No. 4,386,179.

BACKGROUND

The altered compositions of different polymeric materials provide them with significantly different properties. Modifying a particular molecular composition may allow for the production of a material having specific properties required for a particular use.

Recent work has investigated the possibility of producing a thermoplastic material with elastomeric properties. Elastomers generally take the form of thermoset, as opposed to thermoplastic, polymers. For example, natural and man-made rubbers undergo the necessary step of vulcanization in their production. The resultant cross-linked mass cannot melt under the influence of heat. Rather, it merely burns. Silicone rubbers, having a polysiloxane structure, also undergo cross-linking to produce their elastomeric properties. Again, they do not melt when heated.

In their series of U.S. Pat. Nos. 3,485,787, 3,830,767, 4,006,116, 4,039,629, and 4,041,103, the Shell Oil Company has attempted to provide an elastomer with thermoplastic properties through the use of block copolymer formulations. Typically, a block copolymer has a formula of

A—B—A. (1)

In the thermoplastic elastomers, the middle block B of the copolymer posesses the desired elastomeric properties.

However, unlike the commonly used rubber materials, the elastomeric middle blocks do not cross-link throughout the material to provide an integral mass. Rather, the terminal blocks A provide the requisite cohesion between the macromolecules. These terminal blocks apparently bond together in the usual thermoplastic fashion. In Shell's material, the terminal thermoplastic blocks represent a minor portion of the macromolecules' total weight. Accordingly, they adhere to each other in the form of relatively small particles embedded within the elastomeric mass of the middle B blocks.

For the terminal blocks, Shell typically employs polymers formed from monoalkenyl arenes, of which styrene represents a typical example.

For the middle block B, Shell uses a conjugated diene polymer. Butadiene and isoprene provide examples of the elastomeric middle blocks.

The copolymer may contain more than three blocks suggested by formula (1) above. Thus it may have several interspersed A and B blocks linearly interconnected as

A—B—A—B—A—B. (2)

Alternately or additionally, the block copolymer may have blocks with a branched connection to the main chain as

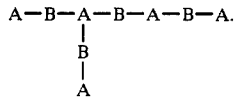
(3)

or, it may have a simple A—B structure. In the ensuing discussion, the simple formula (1) will encompass all of these variations with B representing the elastomeric block. The letter A will designate the thermoplastic binding block which constitutes the terminal blocks on a three-block molecule. The block copolymers may include various other ingredients such as mineral oil, polystyrene polypropylene and antioxidants.

In their U.S. Pat. No. 3,485,787, assigned to Shell, W. R. Haefele et al. incorporate mineral oil to extend the block copolymer. In this particular patent, the middle elastomeric block undergoes hydrogenation to produce an ethylene-butylene block from a butadiene block. To prevent bleeding of the extending oil, N. J. Condon, in U.S. Pat. No. 3,830,767, incorporates a petroleum hydrocarbon wax into the block copolymer.

R. J. G. Dominguez, in Shell's U.S. Pat. No. 4,006,116, and G. R. Heimes et al., in U.S. Pat. No. 4,039,629, create blends of styrene-ethylene-butylene-styrene block copolymers having different molecular weights for both the styrene end blocks and the ethylene-butylene middle blocks. These blends apparently produce a product having superior characteristics for their intended footwear use.

S. Davidson et al., in their U.S. Pat. No. 4,041,103, blend a styrene-ethylene-butylene-styrene block copolymer with a polyamide polymer. The patent states that the product achieves improved dimensional stability at high temperatures.

Notwithstanding the various efforts to produce a high quality thermoplastic elastomer, the resulting materials do not display many of the qualities associated with the usual rubber materials. For example, when extended the thermoplastic elastomers do not have the surface smoothness nor the elasticity of the natural, manmade, or silicone rubbers.

A particular need for an improved thermoplastic material, especially with elastomeric properties, appears in the medical field. Notwithstanding the array of available plastics, the problems of toxicity, incompatibility, surface roughness, lack of flexibility, and others have not submitted to a completely satisfactory solution.

D. H. Kaelble, in U.S. Pat. No. 4,123,409, provides a thermoplastic elastomer primarily for sealing a stoma passing through human tissue. The material utilizes a block copolymer having thermoplastic terminal blocks and an elastomeric intermediate block. The copolymer receives an equal amount of high molecular-weight oil compatible and associatable with the elastomeric block of the copolymer. Thus, a copolymer having a hydrocarbon elastomeric block will incorporate a hydrocarbon mineral oil in order to achieve its desired improvement. Similarly, where a polysiloxane represents the elastomeric block, a silicone oil forms part of the end product. The resulting materials, according to the patent, display an increased pliancy as well as an ability to wet skin.

R. K. Bernstein et al, in their U.S. Pat. No. 3,034,509, add about 0.15 to 1.00 percent by weight of a silicone oil to polyethylene used in surgical tubing. The addition of the silicone oil reduces the blood's toxic reaction to the tubing. It also helps retard blood coagulation where the tubing contacts living tissue for extensive periods of time.

The endotracheal tube represents a further medical device which also receives a substantial investment of time and effort to improving it. The problems associated with an endotracheal tube receive a discussion in W. Wu et al., *Critical Care Medicine,* 1, 197(1973), U. Nordin, *Acta Otorlaryngol Suppl.,* 345, 7(1975), and W. N. Bernhard et al., *Anesthesiology,* 48, 413(1978). These articles focus on the inflatable cuff surrounding the main shaft of the endotracheal tube. The cuff securely lodges the endotracheal tube within the patient's trachea at the location determined by the anesthesiologist. Further, the cuff should completely fill at least a portion of the trachea to prevent aspiration fluids, such as saliva, from passing through the trachea to the patient's lungs.

Two types of cuffs currently find use on endotracheal tubes. The less preferred cuff utilizes a relatively inflexible, or low compliant, material. When deflated, it has a low residual volume. The "low-volume" cuff requires a large internal inflating pressure in order to expand its walls to make contact with the trachea. Any inflation beyond the point of this minimal contact generally results in the exertion of a very large pressure against the tracheal wall. This large lateral wall pressure can so seriously damage the trachea that the patient's death may in fact result.

The second type of endotracheal tube uses a cuff having a highly compliant wall and, when deflated, a large residual volume. One method of forming the high volume cuff involves placing a low volume cuff formed of polyvinylchloride in boiling water. Overinflating the cuff stretches the low volume cuff to form the large cuff.

Excessive inflation of the high volume endotracheal tube in actual use results in the exertion of less lateral wall pressure against the trachea than the low volume type. Nonetheless, the high volume endotracheal tube can still severely damage the patient's trachea. And, since it contacts a larger area of the trachea, its deleterious effects damage more of the trachea than the lower volume models.

Moreover, the deflation of the high volume cuff produces folds in the cuff's wall, a phenomenon referred to as "pruning". When expanding within the trachea, the high volume cuff does not normally expand to its full dimension. If it did, it would then exhibit the same deleterious effects as the low volume cuff. However, expansion to less than its full volume results in the cuff's wall retaining at least some of its folds. These folds, however, provide channels for the aspiration fluids to pass into the patient's lungs. The wrinkles also leave deep grooves in the trachea's mucosal lining.

Generally, the cuffs of the endotracheal tubes have a polyvinylchloride composition which, with its rough surface, can irritate the patient's trachea. Furthermore, the polyvinylchloride includes plasticizers which can leach and induce toxic reactions.

Other cuffs on endotracheal tubes have a latex or a silicone rubber composition. Both of these represent thermoset materials which require dipping and lengthy curing. As a consequence, both have nonuniform surfaces which can also irritate the trachea. Moreover, they can have pinholes and generally display a high rejection of the final product. Moreover, a thermoset plastics, a rejected item cannot undergo salvage and reuse.

Further, each product must undergo thorough testing to assure that it meets the necessary standards. Even with a perfect product, the rubber materials display substantial gas permeability. As a consequence, the internal pressure of the cuff can increase or decrease depending upon the surrounding atmosphere in the trachea. Either event would, of course, produce deleterious consequences. Increasing the pressure further irritates the trachea; decreasing the pressure may allow for the leakage of aspiration fluids around the cuff.

U.S. Pat. No. 4,154,244, to L. F. Becker et al. suggests using a block copolymer similar to the Shell materials above for both the tube's shank and cuff. Specifically, Becker et al. utilize different formulations of the styrene-ethylene-butylene-styrene block copolymer to achieve the different properties of the inflatable cuff as opposed to the substantially rigid shank. Moreover, the material has a rough surface which can irritate the patient's trachea. Also, the composition does not extrude into extremely thin sections which would provide the cuff with the desired high degree of pliancy. Accordingly, the search for improved materials for endotracheal tubes continues.

SUMMARY

An elastomeric thermoplastic hydrocarbon block copolymer with polysiloxane dispersed substantially uniformly throughout posesses physical and surface properties previously provided only by vulcanized, or cross-linked, rubbers. The composition with the polysiloxane and the copolymer submits to processing and extrusion to a thinness not previously achieved with hydrocarbon block copolymeric thermoplastic elastomers.

Dispersing polysiloxane throughout a thermoplastic elastomeric hydrocarbon results in a composition which can display a remarkably smooth surface. Specifically, the surface may have a smoothness comparable on a microscopic scale to that of silicone rubber.

Typically, the composition may include from 0.1 to 8 percent or more of the polysiloxane. This represents an unusual result primarily because of the dissimilar nature of the polysiloxane molecule compared to the hydrocarbon backbone of the elastomeric macromolecule.

The polysiloxane content of the composition becomes even more unusual where the latter already includes an appreciable amount of mineral oil. In fact, the mineral oil may even represent 60 percent of the composition's total weight. Nonetheless, the composition appears able to take up the appreciable amount of polysiloxane and achieve the beneficial results.

The composition may contain up to 25 percent polystyrene and also include other additives such as polypropylene, generally in an amount less than 45 percent of the total weight of the composition. Adding barium sulfate will impart an opacity to X-rays to the composition. Foaming agents may also allow the composition to take the form of a cellular density product.

The block copolymer may have an A—B or preferably A—B—A configuration in which A takes the form of a monovinyl arene polymer block. To provide the elastomeric properties, B may be a hydrogenated or nonhydrogenated conjugated diene polymer block.

The styrene-ethylene-butylene-styrene macromolecule represents a prime example of this type of block copolymer. In it, the styrene blocks typically constitute about 20 to 35 percent of the copolymer's weight while the ethylene-butylene block provides the remaining 65 to 80 percent. The styrene blocks themselves normally have a molecular weight in the range of 5,000 to 40,000. The ethylene-butylene block has a molecular weight greatly exceeding that of the styrene blocks and falling within the approximate range of 20,000 to 500,000. The total molecular weight typically ranges from 50,000 to 600,000.

The polysiloxane, when preferably in the form of silicone oil, has a viscosity within the range of about 20 to 13,000 centistokes. More conveniently, the viscosity should measure about 200 to 500 centistokes. Polysiloxane has the general formula of:

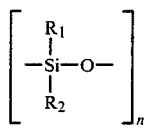

wherein $R_1$, $R_2 = H$, $CH_3$, or

preferably the second of these.

Preparing the elastomeric composition with polysiloxane involves forming a mixture of the elastomeric thermoplastic hydrocarbon block copolymer with silicone oil. This mixture then receives sufficient heat to melt the copolymer. The application of a shearing pressure to the melted mixture intimately combines the components to produce the elastomer. The steps of heating the mixture and the application of the shearing pressure usually take place in an extruder. Increasing the pressure applied to the melted mixture appears to improve the properties of the final product. The extruder may even have a large portion, for example 40 percent, of the flights on its screw in its metering section and a compression ratio of 4 to 1 or even greater. The pressure thus applied to the melted mixture may well approach 1,500 p.s.i., 2,500 p.s.i., or even much higher.

The elastomeric composition with the silicone oil may find use in various types of medical devices. The silicone oil appears to improve the suitability of the elastomer for long term contact with human tissue.

One of the medical devices which can employ the silicone oil-containing hydrocarbon elastomer includes a shaft in the form of an elongated hollow tube through which fluid can pass. An inflatable fluid-tight container surrounds the tube between its ends. Located near one of the tube's ends, it anchors the tube at a particular location in the patient's body. An endotracheal tube represents this type of medical device.

The device must then also have a pressure means to introduce an inflating fluid pressure into the container. It must do so without acccess to the end near which the container sits. Generally, the container and the end closest to it have a location inside the patient's body which, of course, prohibits any access to it. Usually, this pressure device takes the form of a canal running inside of the wall of the main shaft of the device. The container, or cuff, may advantageously have a composition of a thermoplastic elastomeric hydrocarbon block copolymer having polysiloxane distributed substantially uniformly throughout.

The block copolymer with the silicone oil appears extremely inert to human tissue. Thus, the inflatable container of an endotracheal tube can remain in contact with the tracheal wall without irritation due to toxic reactions.

Furthermore, the greater elastic compliancy in thin sections possessed by the material allows for its inflation past the pressure where it seals against the trachea. Minimizing the lateral wall pressure, this material avoids many of the complications induced by other endotracheal tubes currently in use.

The great elasticity of the silicone-containing copolymer along with its low residual volume allows it to expand uniformly against the tracheal wall to provide a complete seal. Thus it prevents the aspiration of fluids into the patient's lungs.

Moreover, its elasticity also permits the container wall, upon deflation, to contract tightly against the tube's shaft without developing folds. In addition, the material has an extremely smooth surface. Together, these features help avoid damage to the tracheal wall upon the insertion, retention, and removal of the device.

Where the device's shaft and the inflatable cuff have compatible compositions which wet each other, a heat seal may suffice to adhere them together. However, the two compositions may lack such compatibility. This represents the situation when using a shaft of polyvinylchloride. In this instance, heat shrinkable plastic sleeves may adhere the silicone-containing polymer to the shaft. Part of the shrinkable sleeves, after going through the heat shrinking process, should then contact the shaft itself. A bead of cement then assures a tight seal between the sleeves and the tube's main shaft.

The improved processing qualities imparted by the silicone oil to the elastomeric, thermoplastic hydrocarbon block copolymer permit the extrusion of the composition into extremely thin sheets. In fact, the composition may extrude in the form of a web through an orifice having a thickness no greater than about 0.015 inch. In fact, it can extrude properly through an orifice as small as 0.005 inch or less.

Furthermore, the material, even when extruded through the thin orifices, can also experience a pulling force upon it after extrusion to reduce its thickness even further. When extruded in the form of a tube, the material, after extrusion, can withstand an internal air pressure as an aid in retaining the tube's shape.

BRIEF DESCRIPTION OF THE FIGURES

FIG. 5 depicts an extruder screw modified to apply a large shearing pressure to a molten thermoplastic polymer.

FIG. 15 shows a partially broken away view of an endotracheal tube in a patient's trachea where the tube's cuff has a composition of an elastomeric, thermoplastic hydrocarbon block copolymer with dispersed polysiloxane.

FIG. 16 depicts an endotracheal tube of the prior art placed in the patient's trachea and where the tube's cuff has a composition of polyvinylchloride.

DETAILED DESCRIPTION

Adding polysiloxane, or silicone oil, to an elastomeric, thermoplastic hydrocarbon block copolymer accomplishes several distinct and desirable results. Initially, the material displays a substantial improvement in its processibility. This has particular importance when extruding the material into thin webs. Without the polysiloxane, the material appears to have flow and surface properties which cause the molten plastic to form globules upon departing the extruder's orifice.

The tendency of the molten material to agglomerate interferes with its processing in several ways. Initially, the extruded material cannot achieve a high degree of surface smoothness. As the molten material attempts to form globules, the surface becomes characterized with hills, valleys, and even craters. The polysiloxane, by apparently decreasing the surface energy of the molten material, allows the extruded plastic to solidify with a very smooth surface.

Figure 1:
FIG. 1 provides an electron photomicrograph with an enlargement of 2,000X of the surface of an elastomeric, thermoplastic, hydrocarbon block copolymer incorporating 3 percent by weight of dispersed polysiloxane.

FIG. 1 gives an electron photomicrograph of the surface of a thermoplastic elastomeric hydrocarbon block copolymer with dispersed polysiloxane. The photomicrograph, with an enlargement of 2,000X, shows dust particles on the elastomer's surface. The material shown in FIG. 1 has a composition of an A—B—A block copolymer with polystyrene representing the end blocks and ethylene-butylene copolymer as the middle block. It also includes about 50 percent by weight mineral oil, 5 percent polypropylene, possibly polystyrenes and various antioxidants. The Shell Chemical Company of Houston, Tex., sells the basic polymer without the polysiloxane under the designation of Kraton G 2705. The polysiloxane, constituting about three percent by weight of the final composition, was dispersed within the block copolymer according to the process described below. The Dow Corning Company of Midland, Mich., provides the polysiloxane as 360 Medical Grade devolatilized silicone oil.

Figure 2:
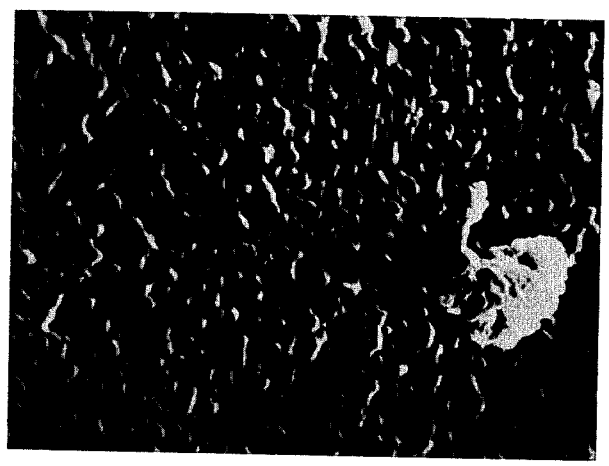
FIG. 2 displays an electron photomicrograph, also at 2,000X, of the surface of a plasticized, polyvinylchloride frequently used to form the cuffs of endotracheal tubes.
Figure 3:
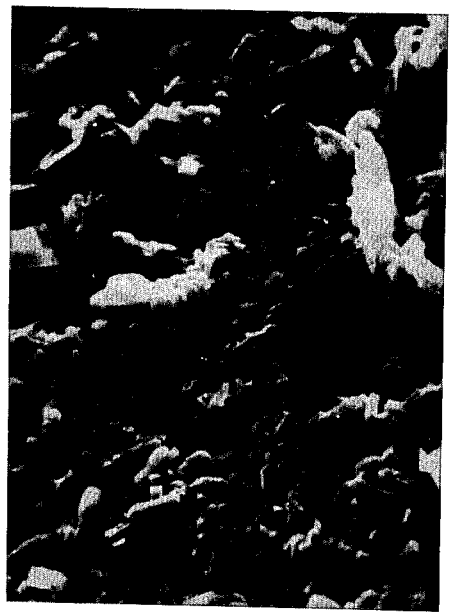
FIG. 3 shows the surface, under 2,000X magnification, of a latex rubber material.
Figure 4:
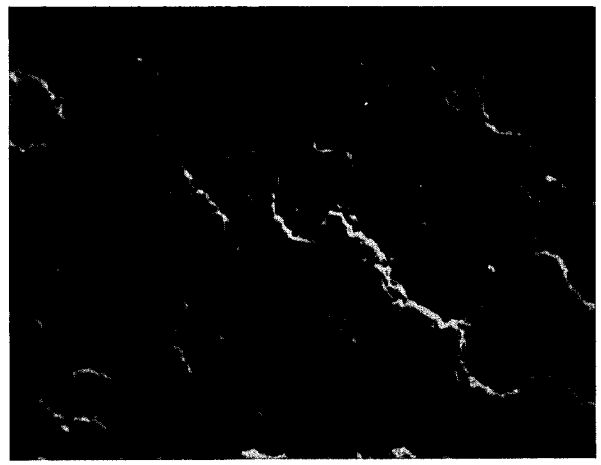
FIG. 4 shows an electron photomicrograph at 2,000X of the surface of silicone rubber.

Comparable photomicrographs showing other materials in common use for medical purposes, especially the cuffs of endotracheal tubes, appear in FIGS. 2 to 4. Each of these has the same magnification as FIG. 1.

Specifically, FIG. 2 shows the surface of an endotracheal tube cuff made of plasticized polyvinylchloride. This composition has found wide use in endotracheal tubes. The photoicrograph readily reveals substantial surface irregularities. This surface roughness irritates and damages the patient's mucosal lining.

FIG. 3 shows the surface, also under 2,000X magnification, of a latex rubber material. Again, the readily apparent surface roughness has an irritating effect upon the patient.

FIG. 4 provides a view of the surface of an endotracheal tube cuff formed of a silicone rubber. The photograph reveals some tendency of the rubber to form globules. Aside from that, the surface appears relatively smooth. A comparison of FIGS. 1 and 4 shows that the thermoplastic hydrocarbon block copolymer with the dispersed polysiloxane has a surface smoothness comparable to or even exceeding that of the silicone rubber.

The surface effects produced by the polysiloxane appear to derive from a slightly increased concentration of silicone molecules at the copolymer's surface. The processing techniques discussed below should typically result in a uniform dispersion of the polysiloxane throughout the block copolymer. However, a slight migration of the silicone molecules to the material's surface occurs. As a result, the material's surface, to a depth of about 5.0 to 20.0 nm., appears to have a concentration of silicone molecules approximately twice that of the bulk of the material. The thinness of this layer, of course, prevents the greater concentration there from affecting the bulk concentration of silicone oil throughout the material. Consequently, on a macroscopic scale, the material has a substantially uniform dispersion of silicone oil. Yet, the immediate surface of the material has a greater concentration of polysiloxane. This gives the surface substantially different properties than the hydrocarbon block copolymer without the dispersed polysiloxane.

Both the surface smoothness and concentration of polysiloxane portend a blood compatibility of the material. Both factors reduced the likelihood of the attachment and clotting of blood components to the polymer.

The Shell patents listed in the "Background" section above give a general discussion on elastomeric thermoplastic hydrocarbon block copolymers. The information given in those references, as well as Shell's U.S. Pat. No. Re. 27,145 of R. C. Jones, has general applicability to the discussion of thermoplastic rubbers below.

Typically, the middle, or B, block of the A—B—A elastomeric hydrocarbon block copolymer provides the molecule with its elastomeric properties; the B blocks themselves possess the rubber qualities. Polymers formed from conjugated dienes have found favor in this role. Butadiene and isoprene represent monomers which, after polymerization, have provided the middle, elastomeric block. Furthermore, the butadiene block may undergo hydrogenation to become an ethylene-butylene copolymer elastomeric block.

The resulting block copolymer typically has its mechanical properties determined primarily by the elastomeric, B block. Accordingly, the middle block should provide at least a majority of the block copolymer's total molecular weight. In fact, it usually provides 65 to 80 percent of the molecular weight of the final product. The molecular weight of the middle, B block usually falls within the range of 20,000 to 500,000 and typically comes within the narrower range of 20,000 to 200,000.

The terminal, or A, blocks of the copolymer provide the cohesiveness between the individual macromolecules in the thermoplastic rubber. These terminal blocks themselves behave as a thermoplastic. They do not usually display any elastomeric quality. However, representing a minority of the weight of the final elastomer, they do not impart their own mechanical properties to the product.

The thermoplastic adherence between molecules of the A blocks replaces the vulcanization of the natural, latex, or silicone rubbers. In vulcanization, actual chemical bonds develop between the macromolecules constituting the rubber. These crosslinking reactions generally occur at elevated temperatures and thus impart the name "thermoset" to the materials. These rubbers generally require extensive periods of time to "cure" or undergo the required crosslinking. The crosslinking does not represent a reversible process. As a consequence, the nonthermoplastic rubbers, once cured to a particular form, cannot melt to adapt a different form. At elevated temperatures they only oxidize or, in more extreme cases, burn.

The terminal A blocks of the block copolymer adhere to each other through physical attraction bonds characteristic of all thermoplastics. Thus, when in the solid form, the terminal blocks of several molecules adhere to each other to provide the required cohesiveness throughout the material. The adhered terminal blocks form small groups, or "particles", embedded within the predominant elastomeric portions of the material. These particles serve to bind the sundry macromolecules in the mass into an integral whole.

At elevated temperatures, these "particles" of physically bonded terminal blocks of different macromolecules actually melt. The entire mass of material then assumes the liquid or molten state and can undergo the usual processing techniques such as extrusion, blow molding, or injection molding. When cooled, the terminal blocks of different macromolecules again physically bond to each other and form particles. The material then generally retains the shape it possessed when the particles formed by the terminal A blocks coalesced into the solid state.

The class of molecules labelled monovinylarenes have provided suitable thermoplastic terminal A blocks for these polymers. Examples of the monomers which can polymerize into the terminal blocks include isoprene and alphamethyl isoprene. The former of these two has generally received greater use.

The terminal S blocks generally have a molecular weight within the range of 5,000 to 40,000, and most fall within the range of 8,000 to 20,000. The terminal blocks constitute about 20 to 35 percent of the total weight of the macromolecule.

As discussed above, the elastomeric block copolymer molecule may include more than two or the three blocks suggested by the A—B—A formula. The macromolecule may contain additional blocks arranged in either the linear or branched fashion suggested by the formulae (2) and (3). In this eventuality, the thermoplastic S block may not actually represent the terminal blocks at all ends of the molecule. In any event, the macromolecule generally has a total molecular weight falling within the range of 50,000 to 600,000.

The silicone oil, or polysiloxane, has the general formula of

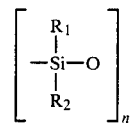

where $R_1$, $R_2$ = H, $CH_3$, or

The readily available silicone oils generally employ the methyl group for both of the radicals $R_1$ and $R_2$.

The viscosity of the polysiloxane should permit its facile coating of and mixing with the crumbs or pellets of the elastomer. This results in a general requirement that it fall within the range of about 20 to 13,000 centistokes. At the lower end of the range, the oil encounters some difficulty in coating the polymer pellets. Silicone oil having a viscosity of 200 to 500 centistokes works well without complication.

Where the final product will have a medical use, a medical grade silicone oil would appear indicated. Furthermore, devolatilizing the silicone oil prior to its introduction to the polymer removes very low molecular weight elements that could leach and irritate the patient's tissues.

The silicone oil generally constitutes about 0.1 to 8 percent of the total weight of the elastomeric composition. In fact, it preferably ranges from 1 to 7 percent. The ability of the hydrocarbon to take up this amount of silicone oil is surprising; the hydrocarbon backbone of the polymer has a drastically disparate nature as compared to the silicone structure of the polysiloxane.

The surprise becomes even greater for polymeric compositions that already include substantial amounts of mineral oil as a lubricant. Mineral oil, if present, may account for up to 60 percent of the total weight of the composition. Typically, the mineral oil constitutes from 25 to 50 percent of the composition's total weight.

Furthermore, the mineral oil and the silicone oil also have distinctly different chemical properties. The former has a hydrocarbon composition as compared to the silicone of the polysiloxane. Moreover, the mineral oil fills the spaces that would presumably accomodate the silicone oil. Yet, a composition having 50 percent of mineral oil can still assimilate several percent of the silicone oil and produce a drastically different elastomer.

Adding polypropylene as a binder to the elastomeric composition produces a stiffening effect upon the elastomeric composition. The polypropylene also reduces its elasticity slightly. The amount of added polypropylene generally remains less than 45 percent of the composition's total weight. It more usually falls within the range of 2 to 20 percent or in the narrower range of 5 to 10 percent.

The addition of $BaSO_4$ also stiffens the polymeric composition. The $BaSO_4$, of course, also provides the polymeric composition with an opacity to X-rays. Titanium dioxide pigment can also affect the polymer's visual appearance. Polystyprene can help the polymer's rheological properties.

Adding a foaming agent to the polymer during its formulation will give a drastically different type of product. Rather than a substantially solid material, a cellular product filled with air and a drastically reduced density will result. This cellular thermoplastic elastomer will have the general feel of a sponge. Employing a nontoxic foaming agent will allow the medical use of the resulting product. One such nontoxic foaming agent is azobisformamide. Added in the amount of about two percent, it creates $CO_2$ gas. The bubbles of gas, covered by the molten elastomer, produce, after solidification, the sponge-like material. This foamed produce may find use as a padding placed on wounds.

Preparing the elastomeric composition with the dispersed polysiloxane begins with the hydrocarbon block copolymer. The techniques for preparing the elastomeric thermoplastics appear in many references including the patents referenced above. The inclusion of the usual additives also appears in these discussions.

Mixing the crumbs or pellets of the elastomeric resin with the polysiloxane should result in a coating of the former with the latter. Placing the pellets or crumbs with the oil in a tumbler assists in attaining a uniform oil coating. Any additional ingredients, such as polypropylene, polystyrene, or $BaSO_4$, may also join the mixture at this point.

The coated elastomer pellets or crumbs next receive sufficient heat to induce their melting. Applying a shearing pressure to the melted coated crumbs or pellets appears to induce a substantially uniform dispersement of the polysiloxane throughout the elastomer. The heat required to effectuate the melting, of course, depends upon the individual elastomer. Typically, it ranges from 160° C. to 225° C.

A pressure of 1,500 p.s.i. should generally insure adequate dispersement of the polysiloxane in the elastomer. Increasing the pressure, however, seems to result in even further improved properties of the product. Thus, the molten mixture may receive the application of a pressure of 2,500 p.s.i., 3,000 p.s.i., or higher.

An extruder provides the most convenient means of achieving the temperatures and pressures required to disperse the polysiloxane within the polymer. An extruder typically has several temperature zones and thus can pass the crumbs or pellets of the polymer through the temperature stages required for melting.

However, the standard extruder may lack the ability to apply sufficient pressure to assure the complete dispersement of the polysiloxane in the polymer. FIG. 5 shows an extruder screw generally at 20 modified to apply a greater shearing pressure to the resin material.

The screw 20 has the three zones characteristic of most extruder screws. The first section 21, known as the feed zone, initiates the melting of the polymer pellets and moves them along to the compression or transition zone 22. There the polymer generally completely melts and undergoes a sufficient shearing stress to mix the ingredients together. The metering section 23 usually provides the melted resin to the die at a known rate and pressure.

The screw shown in FIG. 5 has a length-to-diameter ("L/D") ratio of 24:1. In this type of screw, the metering section 23 typically has about 20 to 25 percent of the total flights, or pitch lengths, of the entire screw. On the modified screw 20 shown in FIG. 5, the metering section 23 has ten flights 24 of the screw's total of 24.62 flights; the feed section 21 has 6.62 flights 27, and the transition section 22 has eight flights. Thus, for the screw 20, the metering section 23 has 40 percent of the total flights. This large fraction of the flights increases the length of time that the resin remains in the metering section 23 and the amount of pressure applied to it.

Furthermore, as shown in FIG. 5a, the flights 24 of the metering section 23 have a much smaller cross-sectional area than the flights 27 of the feed section 21. In fact, the depth 28 of the feed-section flight 27 amounts to four times the depth 29 of the metering-section flight 24. This high compression ratio of 4:1 drastically increases the pressure applied to the material in the metering section 23. To increase the pressure even further, the compression ratio of the feed-section flights 21 to those in the metering section 23 may even go to 5:1 or higher. As this ratio increases, the material becomes squeezed into the smaller flights 24 and, thus, experiences a greater shearing pressure.

Naturally, the pressure experienced by the polymer in the flights 24 also depends upon the size of the orifice through which it passes when departing the extruder. At the smaller orifice sizes of 0.015, 0.010, or even 0.005 inch, only a small amount of resin leaves the extruder over a period of time. The remainder backs up against the orifice opening and maintains the pressure upon the polymer in the pump section 23.

Larger orifices, of course, allow the pressure in the metering section 23 to dissipate. However, placing a screen, called a breaker plate, adjacent to the screw's torpedo section 30 can retain a sufficient back pressure on the metering section 23. This screen can have a mesh of 100 or finer.

Placing additional obstacles in the path of the molten polymer beyond the breaker plate can also increase the pressure experienced in the metering section 23. Furthermore, a longer land, which is the distance along which the bore of the extruder narrows down to the orifice size, can also retain the desired pressure in the flights 24. A pressure blender and a mixing head can also give increased pressure. An extruder with the appropriate modification can deliver the resin to its die under a pressure of 3,000 p.s.i. at the breaker plate.

Extruders produced by two separate manufactuers have adequately mixed the polysiloxane with the block copolymer. The first, a Brabender extruder, employs a ¾ inch, 5:1 compression ratio screw operating at 20 to 105 r.p.m. Its three zones remained at 180° C. while the die was at 170° C. It produced a two-inch sheet of polymer with a width of 0.020 inch.

An HPM extruder (of the HPM Corporation of Mt. Gilead, Ohio) utilized a 2½ inch screw with a 4:1 compression ratio. The screw operated at 10 to 50 r.p.m. and its zones maintained temperatures of 188° C. to 193° C. The die temperature remained at 200° C.

The following examples utilized the polystyrene-ethylene-butylene-polystyrene (SEBS) polymer with a mineral oil lubricant sold as Kraton G 2705 by the Shell Chemical Company. The polymer pellets slowly received the silicone oil and the mixture tumbled together until the pellets achieved a uniform oil coating. Any additional ingredients, such as $BaSO_4$ or polypropylene, were sifted into the mixture at this point. The final mixture with all the ingredients then entered the hopper of the extruder which conveys it to its feed section.

In the following examples, the amounts of the ingredients are expressed as by weight percent. Furthermore, for the tensile strengths, standard die-punched dumbell specimens underwent testing at room temperature on an Instron tensile tester at 20 inches per minute.

EXAMPLES 1 TO 7

The Brabender extruder received mixtures of the Kraton G 2705 SEBS resin pellets and 2 to 5 percent silicone oil. The particular oil used had a viscosity of 350 centistokes at room temperature and had undergone devolatilization prior to its use. The Dow Corning Company of Michigan provides this oil under the designation 360 Medical Grade.

To prepare an elastomer having 2 percent polysiloxane, 3 lbs. of the SEBS pellets received 27.21 gm. of the silicone oil. The extruded material ranged in thickness from 0.016 to 0.018 inch and displayed a 100 percent elasticity modulus of 280 p.s.i.

The elongation and tensile strength of this 2% product appear in Table 1 along with the elastomers having 3, 4, and 5 percent silicone oil. In these latter examples, 40.82 gm., 54.43 gm., and 68.04 gm. of silicone oil, respectively, were added to the 3 lbs. of elastomer pellets.

Examples 2, 4, and 7 were performed at a different time than the others appearing in Table 1. The difference in these results for these materials may indicate a different pressure within the extruder. The material in these examples had a 100 percent elasticity modulus of 300 p.s.i.

TABLE 1

| Example | % Si Oil | % Elongation | Tensile p.s.i. |
|---|---|---|---|
| 1 | 2 | 800 | 2090 |
| 2 | 2 | 710 | 2300 |
| 3 | 3 | 650 | 1930 |
| 4 | 3 | 700 | 1960 |
| 5 | 4 | 560 | 1800 |
| 6 | 5 | 590 | 1690 |
| 7 | 5 | 710 | 1680 |

In heat seal tear tests performed on ½ inch guage material at 2 inches per minute, the polymer of Example 2 with 2% silicone oil tested at 4.1 lbs./inch with 130 p.s.i. The material of Example 4 with 3% polysiloxane tested at 2.9 lbs./inch and 70 p.s.i.

EXAMPLES 8 AND 9

The SEBS pellets, in addition to the silicone oil, also received 5% polypropylene with a melt flow of 12 according to ASTM Standard D-1238-70 and sold by Shell under the designation 5820. For the first of these runs, the same Brabender extruder as above received 3 lbs. of the SEBS pellets, 40.82 gm. of the silicone oil described above, and 58.04 gm. of the polypropylene. The extruded material ranged in thickness from 0.015 to 0.017 inch and displayed a 100 percent elasticity modulus of 300 p.s.i.

Increasing the amount of silicone oil from 3 to 5 percent (54.43 gm.) provided a material having an increased elongation and the same tensile strength. Table 2 provides the results.

TABLE 2

| | 5% Polypropylene | | |
|---|---|---|---|
| Example | % Si Oil | % Elongation | Tensile p.s.i. |
| 8 | 3 | 620 | 2090 |

TABLE 2-continued

| | 5% Polypropylene | | |
|---|---|---|---|
| Example | % Si Oil | % Elongation | Tensile p.s.i. |
| 9 | 4 | 690 | 2090 |

EXAMPLES 10 TO 12

For the following examples, mixtures were prepared having 3 lbs. of the SEBS resin pellets and 204.12 gm. (15%) BaSO$_4$. The amount of silicone oil in these mixtures varied from 3% (40.82 gm.), 4% (54.82 gm.), to 5% (58.04 gm.). The sheets produced by extruding these mixtures ranged in thickness from 0.014 to 0.016 inch and had a 100 percent elasticity modulus of 310 p.s.i. The elongation and tensile strength of these products appear in Table 3.

TABLE 3

| | 15% BaSO$_4$ | | |
|---|---|---|---|
| Example | % Si Oil | % Elongation | Tensile p.s.i. |
| 10 | 3 | 580 | 1530 |
| 11 | 4 | 650 | 1660 |
| 12 | 5 | 640 | 1490 |

EXAMPLES 13 TO 15

The HPM extruder described above with a 2½ inch screw as shown in FIG. 5 appeared to produce material having the most desirable properties. The screw had a 4:1 compression ratio and rotated at 10 r.p.m. The three zones of the extruder operated at 185° C., 193° C., and 199° C., with the die at 204.5° C.

The extruder used a mixture having 2% (45.36 gm.) of the same silicone oil used previously with 5 lbs. of the Shell Kraton G 2705 pellets. The tubular product extruded, in separate runs, to different wall thicknesses. The material had a 100 percent elasticity modulus of 250 p.s.i.

To produce a 0.010 inch wall thickness, the extruder employed a 0.478 inch diameter die with a 0.456 inch pin. The material was drawn down slightly after the extrusion. The percent elongation and tensile strength appear in Table 4 along with tubing having a wall thickness of 0.004 to 0.005 inch and, 0.0025 to 0.004 inch. As shown in Table 4, decreasing the wall thickness reduced the elongation and tensile strength of the tubing.

TABLE 4

| | 2% Si Oil | | |
|---|---|---|---|
| Example | Thickness - inch | % Elongation | Tensile p.s.i. |
| 13 | .010 | 920 | 2320 |
| 14 | .004–.005 | 810 | 1640 |
| 15 | .025–.004 | 610 | 1120 |

The above examples suggest that the polymer formed from the Shell Kraton G 2705 SEBS elastomer with about 2 to 4% silicone oil has the most desirable combination of high strength, low modulus, and maximum elongation. The addition of 5% polypropylene did not change the tensile strength of the produced material.

Adding 15% BaSO$_4$ decreased the tensile strength of the resulting elastomer. The elongation, however, increased. The BaSO$_4$, in the compositions having from 3 to 4% silicone oil, also provided the resulting elastomer with a slight increase in rigidity.

Once produced, the material, as a thermoplastic, will submit to the usual product-forming techniques. Thus, it can undergo further extrusion to a particular shape, if not achieved in the original extrusion. It can also undergo the usual blow-molding techniques. Moreover, its thermoplastic nature allows the reuse of scraps of material and of rejected parts.

The elastomer with the dispersed polysiloxane can have a wide variety of uses. In fact, the only limitation seems to be the ability to conceive of such uses. It can include the mundane, such as food packaging materials or automobile seat covers. In fact, the thermoplastic elastomer with dispersed polysiloxane retains its elastomeric properties at very low temperatures. Thus, it would appear highly suitable for such uses as the suggested food packaging and seat covers.

Moreover, the thermoplastic elastomer with the dispersed polysiloxane can also have sophisticated uses such as medical appliances. Toxicological tests show that materials produced according to the examples given above remain nontoxic when in contact with human tissue. Furthermore, no negative effects from leaching occurred during a period of seven days of testing. Thus, they can also find use as objects implantable in the human body.

Figure 6:
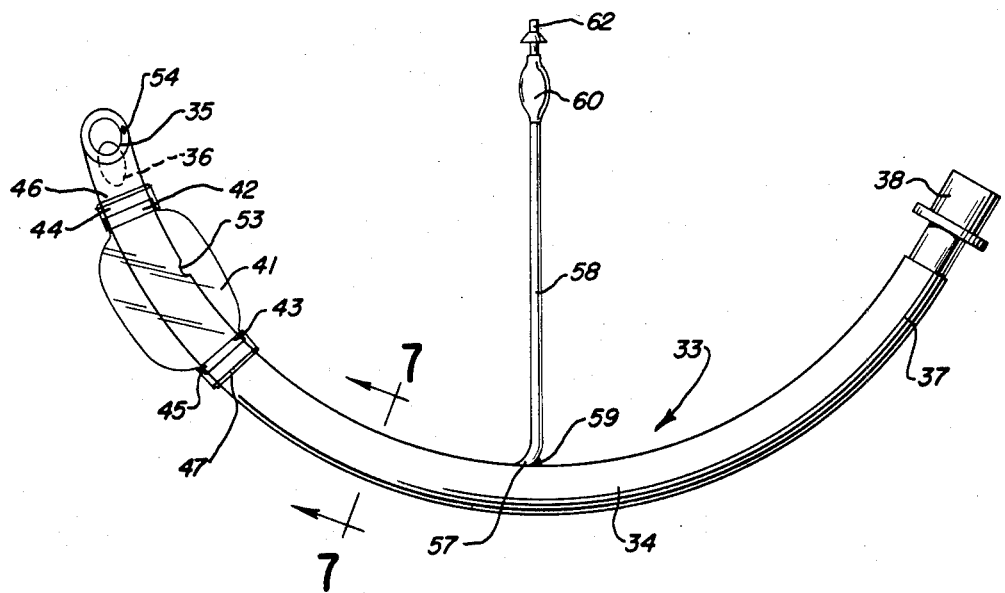
FIG. 6 gives an endotracheal tube having an inflatable cuff formed from an elastomeric, thermoplastic hydrocarbon block copolymer with 4 percent by weight dispersed polysiloxane.

In particular, medical devices having an inflatable balloon on a central shaft can take advantage of the thermoplastic elastomer having dispersed polysiloxane. The endotracheal tube, appearing generally at 33 in FIG. 6, provides one example of this type of medical appliance.

The endotracheal tube 33 includes the main shaft 34. The shaft 34 in most endotracheal tubes has a composition of a clear, flexible, medical-surgical grade polyvinylchloride. As stated above, an SEBS thermoplastic elastomer may also find use as the shaft 34. The shaft 34 generally has a substantially rigid construction and a permanent, uniform arc generally with a 130 to 140 mm. radius to facilitate its insertion into the trachea.

The shaft 34 may have an inside diameter ranging from 2.5 mm. to 10 mm. Its length ranges from 240 mm. to 360 mm. depending upon its internal diameter.

The "proximal" end 35 has a 30° to 45° angle and a Murphy tip with the eye 36. The end 35 and the eye 36 provide passageways to both of the patient's bronchi if the attendant inserts the tube 33 that far into the trachea.

The other, or "distal", end 37 of the shaft 34 receives the adaptor 38. It generally has a composition of polypropylene and several companies sell them separately. The adaptor 38 connects to the actual equipment that assists the patient's respiration.

The shaft 34 also carries the inflatable cuff 41. The cuff 41 makes use of the SEBS block copolymer with the dispersed polysiloxane generally described above. The preferred cuff uses the Shell Kraton G 2705. The SEBS polymer in this formulation has 28% styrene and 72% ethylene-butylene. Additionally, it has 5% polypropylene and 45% mineral oil. To make the cuff, the resin receives 4% polysiloxane. The tubing for the cuff 41 typically has a thickness of 0.008 to 0.010 inch.

Having an air-tight compartment with this tubing requires the sealing of the ends 42 and 43 of the cuff 41 to the shaft 34. If the shaft 34 has a composition of the same SEBS block copolymer as the cuff 41, they can adhere to each other through a heat weld. Thus, sonic welding, for example, will melt the ends 42 and 43 and the adjacent portions of the shaft 34. The molten material from the components can then comingle, and, when cold, adhere to each other. In general, the heat sealing of the cuff 41 to the shaft 34 can occur when the materials of these two components are compatible; when melted, they wet each other.

However, the polyvinylchloride of the shaft 34 lacks compatibility with the SEBS block copolymer of the cuff 41. Accordingly, they lack the compatibility to heat seal to each other. To seal the cuff 41, the shrink sleeves 44 and 45 compress the cuff's ends 42 and 43 against the shaft 34. The shrink sleeves 44 and 45 represent short lengths of clear polyvinylchloride shrinkable tubing. The Gilbreth International Corporation sells this material in a medical-surgical grade as "Skin Tight 430RK". The material, when heated to 300° F. for 3 sec., forms an air-tight sealing collar around the ends 42 and 43 of the cuff 41 against the shaft 34.

The shrink sleeves 44 and 45 normally suffice to retain the cuff 41 in position and provide an air-tight seal around the ends 42 and 43 of the cuff. However, the beads of cement 46 and 47 maintain the seal. The cement includes one part by weight of clear 85 duro Food and Drug Administration (FDA) surgical grade polyvinylchloride (PVC) dissolved in five parts of tetrahydrofuran. This mixture then receives seven parts of methyl isobutyl ketone to prepare the final cement. This PVC-based cement will adhere to the polyvinylchloride of both the shaft 34 and the shrink sleeves 44 and 45. After the sleeves 44 and 45 have shrunk to provide an air-tight seal of the cuff 41, the beads of cement 46 and 47 are placed at the junctures of the sleeves 44 and 45 at the shaft 34.

Figure 7:
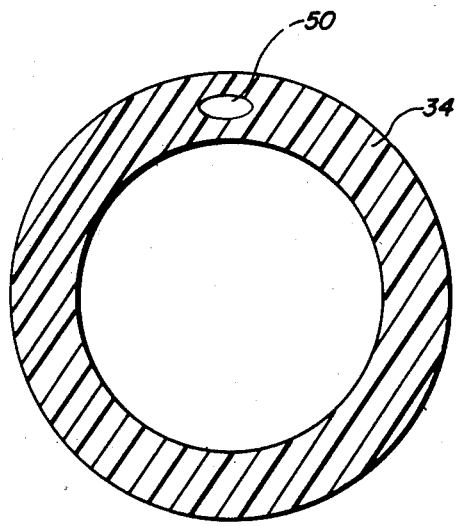
FIG. 7 gives a cross-sectional view along the line 7—7 of the shaft of the endotracheal tube of FIG. 6.

Once placed inside the patient's trachea, the cuff 41 must receive an inflating fluid, usually air, in order to lodge it against the patient's tracheal wall. However, the proximal end 35 of the shaft 34 as well as the cuff 41, both inside the patient's trachea, have become inaccessible to direct manipulation by the attendant. Accordingly, the shaft 34, shown in FIG. 7, has the lumen 50 running its entire length. The lumen 50 allows for the introduction of the inflating fluid into the cuff 41.

To permit fluid in the lumen 50 to enter the cuff 41, the shaft 34 has the notch 53 cut into it. The notch 53 has a location on the shaft 34 and a sufficient depth to intersect the lumen 50. Accordingly, fluid within the lumen 50 can enter and inflate the cuff 41.

The rod 54 fills the lumen 50 between the notch 53 and the shaft's end 35. This prevents fluid in the lumen 50 from escaping out the lumen's opening in the shaft's end 35. The rod 54 should have a composition similar to the material of the shaft 34. The rod 54, in particular, has a composition of nontoxic PVC with a 70 duro hardness. It may also include a loading of about 30% $BaSO_4$ to make it opaque to X-rays. This permits the observation of the insertion of the endotracheal tube 33 into the trachea with the aid of an X-ray machine. A small amount of methyl isobutyl ketone facilitates the insertion and seals the rod 54 in the lumen 50.

The shaft 34 includes the second notch 57 which communicates with the lumen 50. The air inflation tube 58 then enters the lumen 50 through the notch 57. A small application of the methyl isobutyl ketone solvent should precede the introduction of the tube 58. This allows the tube 58, made of PVC, to adhere to the interior surface of the lumen 50 and provides a fluid-tight seal. A small drop 59 of the same PVC cement described above firmly adheres the tube 58 to the shaft 34.

The inflation tube 58 connects in turn to the pilot balloon 60 formed of dipped plastisol medical-grade PVC. The balloon, having a highly flexible construction, permits the visible monitoring of the inflation pressure actually entering the cuff 41; as the pressure in the cuff 41 increases, so does the size of the pilot balloon 60.

Finally, the pilot balloon connects to the Roberts' valve 62 obtainable from the Halkey-Roberts Corporation. Designated as Roberts' valve A10-ACS, it has a vinyl copolymer composition.

The valve 62 accepts a leur-loc syringe. The insertion of the syringe into the valve 62 permits a change in the fluid pressure inside the cuff 41. Specifically, fluid introduced into the valve 62 passes through the pilot balloon 60, the inflation tube 58, the lumen 50, and the notch 53 to inflate the cuff 41. Similarly, a negative pressure created by the syringe attached to the valve 62 aspirates fluid from the cuff 41 through the notch 53, the lumen 50, the inflation tube 58 and the pilot balloon 60.

The cuff 41, after the initial assembly of the endotracheal tube 33, may undergo a forming process prior to its actual use in the patient. Otherwise, the cuff 41 will merely inflate over a very small area intermediate its ends 42 and 43. The forming process results in the cuff 41 inflating over its entire length between the sleeves 44 and 45.

Figure 8:
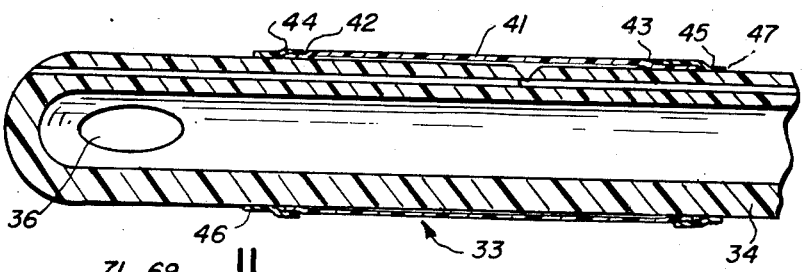
FIG. 8 depicts an endotracheal tube with a cuff formed of an elastomeric thermoplastic copolymer with dispersed polysiloxane prior to the cuff's shaping.

FIG. 8 shows the cuff 41 of the endotracheal tube 33 prior to the final forming and orienting steps. As shown there, the thermoplastic elastomeric tube forming the cuff 41 has a diameter of 0.4 inch, a thickness of 0.008 to 0.010 inch, and a length of 2 inches. The PVC sleeves 44 and 45 each have a length of 0.37 inch and half of each of them contacts the shaft 34 while the other half contacts the cuff 41.

To begin the forming process, the end 35 of the endotracheal tube having the cuff 41 enters the mold shown generally at 66. The mold has two halves 67 and 68 formed of time and heat cured R.T.V. molded silicone. The interior surface 69 of the mold 66 has a cross-sectional configuration generally resembling a cloverleaf. The plane showing the cross-sectional views of FIGS. 9 and 10 passes through the center of the mold, and, thus, the center of the endotracheal tube 33.

The wide discs 71 and 72 of the mold 66 each has a diameter of 4.75 inches. The narrow throat 73 of the mold has a diameter of 2 inches. Furthermore, the end surfaces 74 and 75 have a separation of 2 inches from each other.

With the endotracheal tube inside the mold 68, the fluid enters and inflates the cuff 41 until it contacts the mold's interior surface 69. The inflation occurs with the mold 66 maintained at room temperature.

Figure 9:
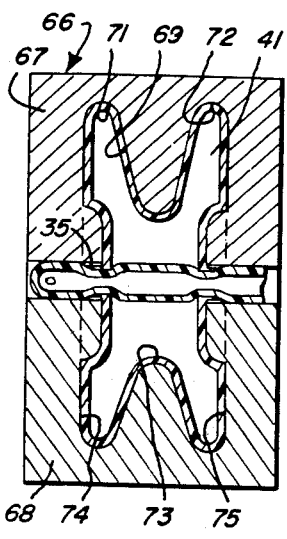
FIG. 9 is the cuff of an endotracheal tube undergoing the first step of an orientation process in a cloverleaf-shaped mold.

During the inflation in FIG. 9, the portions of the cuff in the region 71 and 72 of the mold expand from a diameter of 0.4 inch to a diameter of 4.75 inches. This almost 12-fold expansion of the cuff 41 causes the material to exceed its elastic limits. As a result, it retains a new orientation and shape, when deflated, from the shape shown in FIG. 9.

The exact inflation required to achieve a permanent orientation depends upon the particular elastomer employed. Less elastic material may require an expansion to only 3 times its original size. For other materials, an expansion to 5 to 8 times the original dimension may suffice.

As shown above, the material with the dispersed polysiloxane can undergo an expansion of about 12 times its original size without breaking. Very few other materials, if any, whether thermoplastic or thermoset, can achieve this expansion without substantial and irreparable damage.

Not only does the shape of the cuff 41 undergo alteration during the inflation, so does the thickness of the thermoplastic elastomer forming the cuff. The edges 78 of the cuff 41 remain under the shrink seals 44 and 45 and do not experience any stretching at all. Consequently, they retain their original thickness of 0.008 inch. The cuff portion 79 immediately adjacent to the beginning of the mold 66 undergoes a slight expansion and achieves a thinness, after the first expansion step, of 0.007 inch. The regions 80 of the cuff 41 expand into the legs 71 and 72 of the cloverleaf mold 66 and experience the greatest expansion. As a result, they finish the first inflation step with a thickness of 0.005 inch. The middle 81 of the cuff 41 only expands until it contacts the neck 73 of the mold 66. Its thickness reduces to 0.006 inch.

Figure 10:
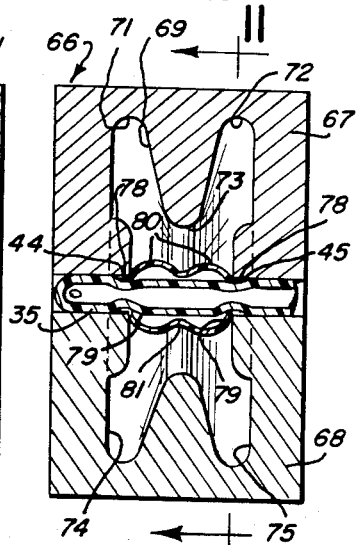
FIG. 10 shows the endotracheal tube of FIG. 8 after it has undergone the shaping process depicted in FIG. 9.
Figure 11:
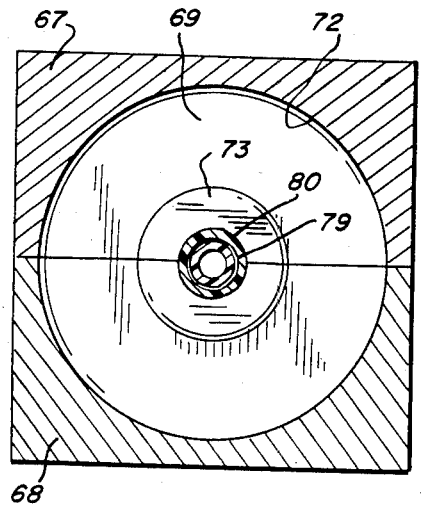
FIG. 11 gives a cross-sectional view along the line 11—11 of the mold and preliminary shaped endotracheal tube of FIG. 10.

If the endotracheal tube underwent use with the cuff 41 having the configuration shown in FIGS. 10 and 11, it would not inflate along its entire length against the patient's trachea. The cuff 41 would experience two principal areas of inflation around the bulges 80 shown in FIG. 10. This would provide two small areas of contact against the patient's trachea, with the middle 81 not also expanding to make contact. Accordingly, the cuff 41 undergoes the shaping step illustrated in FIG. 12.

Figure 12:
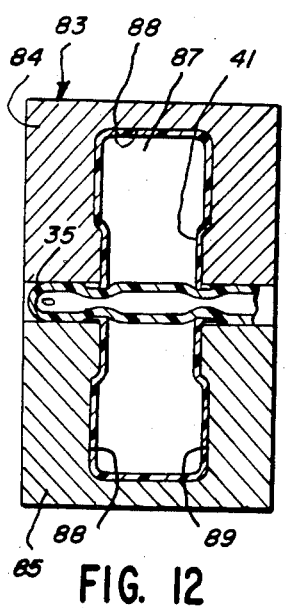
FIG. 12 shows an endotracheal tube undergoing a second shaping step in a rectangularly-shaped mold.
Figure 13:
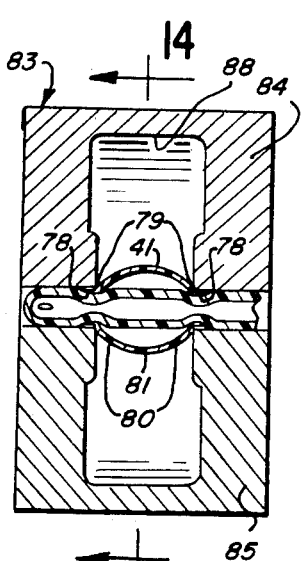
FIG. 13 shows an endotracheal tube that has undergone both the shaping in the cloverleaf-shaped mold in FIGS. 9 through 11 and the second shaping step of the mold in FIG. 12.
Figure 14:
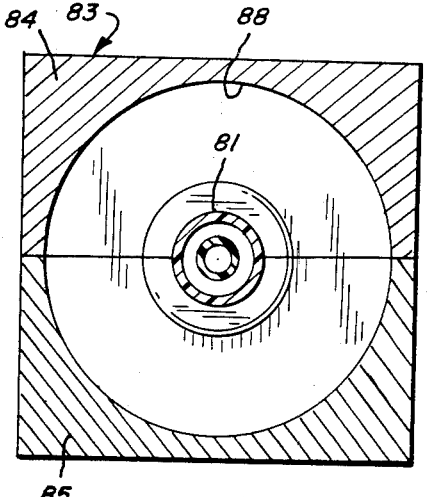
FIG. 14 gives a cross-sectional view along the line 14—14 of the mold and endotracheal tube with shaped cuff shown in FIG. 13.

The mold 83 shown in FIGS. 12, 13, and 14 has the two halves 84 and 85 again made of R.T.V. molded silicone. The end 35 of the endotracheal tube is placed inside the mold 83 with the cuff 41 centered about the hollow cavity 87. With the mold 83 at room temperature, an inflating fluid enters the cuff 41 until it contacts the interior surface of the mold 83. This inflation causes the cuff 41 to expand to a diameter of 4.75 inches to reach the lateral edge 88 of the mold 83.

The end surfaces 88 and 89 of the mold 83 have a separation of 1.8 inches from each other. This is somewhat less than the 2.0 inches of the surfaces of 74 and 75 in the first mold of FIGS. 9 to 11.

After deflation, the cuff 41 retains a residual shape altered by its inflation in the mold 83. This residual shape appears in FIGS. 13 and 14.

As a result of the shaping in the mold 83, the cuff's edges 78 retain their original thickness of 0.008 inch. The portions 79 of the cuff 41 near the edge of the mold experience very little alteration from the mold in FIG. 12 and also retain their thickness of 0.007 inch. The interior portion 80 of the cuff 41, offset slightly from the cuff's center, achieves a thickness of 0.003 inch.

The very middle 81 of the cuff 41 has its thickness reduced to 0.002 inch, approximately one fourth of its original thickness. Thus, the cold-forming process reduces the thickness of the middle of the cuff 41 from 0.008 inch to 0.002 inch. The cold-forming process, in conjunction with the elastomeric, thermoplastic SEBS block copolymer, has produced a stretchable material having a thickness of 1/500 inch.

Moreover, the material has substantial elasticity and strength. Rather than weakening the elastomer, the over-stretching involved in the cold forming appears to improve the strength and elasticity of the block copolymer.

Further, the use of molds in the cold-forming process avoids overstressing the thinner areas in the elastomer. As the cuff inflates, the thinner areas tend to expand preferentially. However, when they contact the mold's interior surface, they expand no further; the mold keeps these areas from continuing to expand primarily; from forming an aneurysm; and from breaking. With the thinner area no longer able to expand, the remaining portions of the material then expand and thin until they too contact the interior surface of the mold. In this fashion, the cold-forming process tends to equalize the thickness of the polymeric material.

The cold-forming process, by utilizing the molds such as in FIGS. 9 to 14, imparts a predetermined accurate design to the elastomeric material. Moreover, since this material neither undergoes heating nor cooling, the process works quickly and achieves a high degree of efficiency.

The endotracheal tube employing a cuff formed from an elastomeric, thermoplastic hydrocarbon block copolymer with dispersed polysiloxane possesses several advantages over the devices previously employed. In general, it results in less injury or discomfort to the patient.

When the cuff 41, as shown in FIG. 13, inflates within the patient's trachea, it has, due to the cold forming, and increased effective area which actually contacts the patient's tissues. This area applies a gentle pressure to the tracheal wall and inflicts less damage than would a small area of the cuff 41, without the cold forming exerting a high pressure against the tracheal wall.

As shown by FIGS. 9 through 14 and as implied by its designation as an "elastomeric" material, the cuff formed of the polymer with dispersed polysiloxane actually increases in size when inflated. Consequently, prior to use, it may have a very small size, and, thus, exhibit a low profile about the shaft of the endotracheal tube. Moreover, it has little or no folding over of material when totally deflated. This configuration of the deflated cuff adhering closely to the device's shaft with minimal or no projections provides a smooth surface to the patient's trachea during its insertion. As a consequence, it creates less patient discomfort or injury when introduced into the trachea.

Moreover, since the cuff begins without substantial folding over, it has none when inflated in the trachea. The endotracheal tube's cuff thus applies a smooth continuous surface against the tracheal wall as seen in FIG. 15. As shown there, the cuff 41 lies smoothly against the tracheal wall 94. It conforms closely to the hills 95 and valleys 96 resulting from the undulations in the tracheal wall. It also expands into depressions formed by irregularities in the tracheal wall. FIG. 16, by way of comparison, shows an endotracheal tube generally at 97 having a cuff 98 formed from polyvinylchloride. The PVC, being nonelastomeric, lies in folds about the tube's shaft even when deflated. Thus, when inflated sufficiently to contact the tracheal wall 94, the cuff 98 still has the folds or creases which run its entire length. This allows for the aspiration of fluids from the patient's mouth, such as saliva, into the patient's lungs. Sufficient fluid passing into the lungs in this fashion can induce pneumonia. The problem becomes especially exacerbated in tracheas having severe deformations and irregularities; the PVC simply cannot follow the shape of the trachea 96. Additionally, the folds 99 leave grooves and sores in the patient's trachea.

Moreover, the stiff polyvinylchloride of the cuff 98 does not conform to the trachea's hills 95 and valleys 96. Consequently, spaces 100 may remain between the tracheal wall 94 and the cuff 99 in the regions of the valleys 96 formed in the tracheal wall. Consequently, the polyvinylchloride exerts its pressure against the small hill areas of the tracheal wall 94. These elevated areas, under increased pressure, readily become sore and traumatized.

As discussed with regards to FIGS. 9 and 12, the cuff 41 formed of the thermoplastic elastomer with dispersed polysiloxane can expand to 12 times its original size without bursting. It can easily inflate to 8 to 10 times its original diameter without adverse effects. This permits it to expand to the size required when used in an abnormally large trachea. Inflating the cuff until it contacts the tracheal wall becomes a safe procedure and provides assurance of a complete sealing of the trachea without bursting or substantial injury to the patient.

Furthermore, the high elasticity of the material results in only minimal increases in the internal pressure of the cuff as its volume increases. Thus, when the cuff reaches a sufficient size to contact the tracheal wall, it still exerts only minimal pressure against the tracheal wall. Consequently, fewer sizes of endotracheal tubes will suffice for the whole range of patients that a hospital encounters. Thus, the hospital can stock fewer sizes and reduce its inventory.

Furthermore, the elasticity of the material results in it exerting only a low pressure against the tracheal wall when inflated to a sufficient volume to seal the trachea. This low pressure avoids the damage caused by the previously used cuffs which exerted a large lateral wall pressure.

Furthermore, the material with dispersed polysiloxane has a smooth, soft surface when inflated. This property, too, results in less irritation and less mucosal damage of the patient's tracheal wall.

The low pressure required to seal the cuff against the tracheal wall and the inherent softness of material with polysiloxane allow it to facilely flex. This property becomes important in light of the fact that respiratory equipment often causes the endotracheal tube to pulsate slightly in and out of the patient's trachea. The soft cuff 41 absorbs this motion. As a result, the cuff 41 does not scrape against the tracheal wall. The PVC cuffs, by comparison, lack this softness and elasticity. As the respirator pulsates, the PVC cuffs actually abrade against the tracheal wall. Having a rough surface, they can and do injure the patient's trachea.

Accordingly, what is claimed is:

1. The composition of matter comprising:
   (A) an elastomeric, thermoplastic hydrocarbon block copolymer, said copolymer having a total molecular weight of about 50,000 to 600,000
   (B) polysiloxane dispersed substantially uniformly throughout said copolymer, having a viscosity of about 20 to 13,000 centistokes, and comprising about 0.1 to 8 percent of the total weight of said composition; and
   (C) mineral oil dispersed substantially uniformly throughout said copolymer and comprising less than about 60 percent of the total weight of said composition.

2. The composition of claim 1 further including polypropylene dispersed substantially uniformly throughout said copolymer and comprising less than about 45 percent of the total weight of said composition.

3. The composition of claim 2 wherein said block copolymer has an A—B—A configuration wherein A is a monovinylarene polymer block and B is a hydrogenated or nonhydrogenated conjugated diene polymer block.

4. The composition of claim 3 wherein:

(A) said block copolymer is a styrene-ethylene-butylene-styrene block copolymer;
(B) said polysiloxane comprises about 1 to 7 percent of the total weight of said composition;
(C) said mineral oil comprises about 25 to 50 percent of the total weight of said composition; and
(D) said polypropylene comprises about 5 to 10 percent of the total weight of said composition.

5. The composition of claim 4 wherein the styrene blocks of said copolymer have a molecular weight of about 8,000 to 20,000 and comprises about 20 to 35 percent of the total weight of said copolymer and the ethylene-butylene block has a molecular weight of about 20,000 to 500,000 and comprises about 65 to 80 percent of the total weight of said copolymer.

6. The composition of matter comprising:
(A) an elastomeric, thermoplastic A—B—A block copolymer, where A is a monovinylarene polymer block and B is a hydrogenated or nonhydrogenated conjugated diene polymer block;
(B) polysiloxane dispersed substantially uniformly throughout said copolymer, having a viscosity of about 20 to 13,000 centipoise, and constituting about 0.1 to 8 percent of the total weight of said composition; and
(C) mineral oil dispersed substantially uniformly throughout said copolymer and comprising less than about 60 percent of the total weight of said composition.

7. The composition of claim 6 further including polypropylene dispersed substantially uniformly throughout said copolymer and comprising less than about 45 percent of the total weight of said composition.

8. The composition of claim 7 wherein:
(A) said block copolymer is a styrene-ethylene-butylene-styrene block copolymer;
(B) said polysiloxane comprises about 1 to 7 percent of the total weight of said composition;
(C) said mineral oil comprises about 25 to 50 percent of the total weight of said composition; and
(D) said polypropylene comprises about 5 to 10 percent of the total weight of said composition.

9. The composition of claim 8 wherein the styrene blocks of said copolymer have a molecular weight of about 5,000 to 40,000 and comprises about 20 to 35 percent of the total weight of said copolymer and the ethylene-butylene block has a molecular weight of about 20,000 to 500,000 and comprises about 65 to 80 percent of the total weight of said copolymer.

* * * * *

UNITED STATES PATENT AND TRADEMARK OFFICE
CERTIFICATE OF CORRECTION

PATENT NO. : 4,552,914
DATED : November 12, 1985
INVENTOR(S) : ROBERT E. STERLING It is certified that error appears in the above-identified patent and that said Letters Patent is hereby corrected as shown below:

ON THE TITLE PAGE

Insert the following terminal disclaimer:

[*] Notice: The portion of the term of this patent subsequent to Nov. 6, 2001 has been disclaimed.

Signed and Sealed this

First Day of April 1986

[SEAL]

Attest:

DONALD J. QUIGG

Attesting Officer

Commissioner of Patents and Trademarks